(12) United States Patent
Fujino et al.

(10) Patent No.: US 11,066,432 B2
(45) Date of Patent: Jul. 20, 2021

(54) ETHER PHOSPHOLIPIDS AND METHOD FOR PRODUCING THE SAME

(71) Applicant: Institute of Rheological Functions of Food, Fukuoka (JP)

(72) Inventors: Takehiko Fujino, Fukuoka (JP); Shiro Mawatari, Fukuoka (JP)

(73) Assignee: Institute of Rheological Functions of Food

( * ) Notice: Subject to any disclaimer, the term of this patent is extended or adjusted under 35 U.S.C. 154(b) by 0 days.

(21) Appl. No.: 15/533,528

(22) PCT Filed: May 13, 2015

(86) PCT No.: PCT/JP2015/063740
§ 371 (c)(1),
(2) Date: Jun. 6, 2017

(87) PCT Pub. No.: WO2016/092878
PCT Pub. Date: Jun. 16, 2016

(65) Prior Publication Data
US 2018/0327433 A1    Nov. 15, 2018

(30) Foreign Application Priority Data
Dec. 8, 2014  (JP) .............................. JP2014-247792

(51) Int. Cl.
| C07F 9/10 | (2006.01) |
| A23J 7/00 | (2006.01) |
| A61K 31/685 | (2006.01) |
| C11B 11/00 | (2006.01) |
| A61K 35/618 | (2015.01) |
| A23L 33/12 | (2016.01) |
| A23L 2/52 | (2006.01) |

(52) U.S. Cl.
CPC ............... *C07F 9/103* (2013.01); *A23J 7/00* (2013.01); *A23L 2/52* (2013.01); *A23L 33/12* (2016.08); *A61K 31/685* (2013.01); *A61K 35/618* (2013.01); *C07F 9/10* (2013.01); *C11B 11/00* (2013.01); *A23V 2002/00* (2013.01)

(58) Field of Classification Search
CPC .. C07F 9/103; A23L 33/12; A23L 2/52; A23J 7/00; C11B 11/00; A23V 2002/00
See application file for complete search history.

(56) References Cited

U.S. PATENT DOCUMENTS

| 9,169,280 | B2 | 10/2015 | Khan et al. |
| 2010/0029966 | A1 | 2/2010 | Fujino et al. |
| 2010/0055277 | A1 | 3/2010 | Nadachi et al. |
| 2010/0160659 | A1 | 6/2010 | Catchpole et al. |
| 2011/0160471 | A1 | 6/2011 | Nadachi et al. |
| 2012/0283223 | A1 | 11/2012 | Ifuku et al. |
| 2013/0172293 | A1 | 7/2013 | Mawatari et al. |
| 2013/0281404 | A1 | 10/2013 | Yazawa et al. |

FOREIGN PATENT DOCUMENTS

| EP | 2308954 A1 | 4/2011 | |
| EP | 2522353 A1 | 11/2012 | |
| EP | 3241884 A1 | 11/2017 | |
| JP | 2006124488 A | 5/2006 | |
| JP | 2007262024 A | 10/2007 | |
| JP | 2008179588 A | 8/2008 | |
| JP | 2009227765 A | 10/2009 | |
| JP | 2009263518 A | 11/2009 | |
| JP | 2009538366 A | 11/2009 | |
| JP | 5062873 B2 | 10/2012 | |
| JP | 2013-053109 | * 3/2013 | .............. C11B 11/00 |
| JP | 201353109 A | 3/2013 | |
| JP | 201353110 A | 3/2013 | |
| JP | 5185539 B2 | 4/2013 | |
| JP | 5357005 B2 | 12/2013 | |
| JP | 5430566 B2 | 3/2014 | |
| JP | 5489439 B2 | 5/2014 | |
| JP | 5774816 B2 | 9/2015 | |
| JP | 5847086 B2 | 1/2016 | |
| JP | 6016363 B2 | 10/2016 | |
| JP | 6025568 B2 | 11/2016 | |
| WO | 2008091015 A1 | 7/2008 | |
| WO | 2008146942 A1 | 12/2008 | |

(Continued)

OTHER PUBLICATIONS

Machine translation of JP 2013-053109, accessed from https://worldwide.espacenet.com, Accessed Feb. 28, 2019.*

Fujino et al., Effects of Plasmalogen on Patients with Mild Cognitive Impairment: A Randomized, Placebo-Controlled Trial in Japan, Journal of Alzheimer's Disease and Parkinsonism, Jan. 2018, pp. 1-5, vol. 8.

International Search Report for Application No. PCT/JP2015/063617 dated Jun. 30, 2015.

Yamashita et al., "Preparation of Marine Plasmalogen and Selective Identification of Molecular Species by LC-MS/MS", Journal of Oleo Science, Apr. 9, 2014, vol. 63, No. 5, pp. 423-430.

(Continued)

*Primary Examiner* — Alicia L Otton (74) *Attorney, Agent, or Firm* — Lerner, David, Littenberg, Krumholz & Mentlik, LLP (57) ABSTRACT

[PROBLEM TO BE SOLVED] It enables any superior ether phospholipids to the conventional ones and a method for producing the same in an easy manner on a massive scale, in light of effects of treating and improving brain diseases such as Alzheimer's disease, Parkinson disease, depression and schizophrenia, metabolic diseases such as diabetes, various infectious diseases, and immune disorders. [SOLUTION] Ether phospholipids are obtained from bivalve tissues such as clams and corbicula by extraction processing. The ether phospholipids exhibit significantly superior effects of the above as compared to the conventional ether phospholipids derived from chicken tissues.

8 Claims, 3 Drawing Sheets

(56) References Cited

FOREIGN PATENT DOCUMENTS

| WO | 2009154309 A1 | 12/2009 |
|---|---|---|
| WO | 2010047404 A1 | 4/2010 |
| WO | 2011083827 A1 | 7/2011 |
| WO | 2012039472 A1 | 3/2012 |
| WO | 2016181491 A1 | 11/2016 |

OTHER PUBLICATIONS

"Anxiety Disorders", Mayo Foundation for Medical Education and Research (MFMER), accessed Jan. 7, 2019, 5 pages. https://www.mayoclinic.org/diseases-conditions/anxiety/symptoms-causes/syc-20350961.

Extended European Search Report and Written Opinion for EP Application No. 15891816.9, dated Nov. 28, 2018.

Hara and Radin, "Lipid Extraction of Tissues with a Low-Toxicity Solvent", Analytical Biochemistry, vol. 90, No. 1, Oct. 1978, pp. 420-426.

American Brain Tumor Association (ABTA) http://www.abta.org/brain-tumor-information/types-of-tumors/glioma.html?print=t, Accessed Mar. 9, 2016, Sep. 2011, 3 pages.

Amiri-Kordestani et al., JNCI J Natl Cancer Inst. vol. 104, Issue 8, Apr. 2012, 2 pages.

Clark, Michelle, "Design and optimization of dosage regimen", Pharmacology: VIII, Lipincott Williams & Wilkins, 2012, p. 23.

Johnson et al., "Relationships between drug activity and NCI preclinical in vitro and in vivo models and early clinical trials", British Journal of Cancer, vol. 84, No. 10, May 2001, pp. 1424-1431.

Patel et al., "Schizophrenia: Overview and Treatment Options", Pharmacy and Therapeutics, vol. 39 No. 9, Sep. 2014, pp. 638-645.

Supplementary European Search Report and Written Opinion for EP Application No. 15867632, dated May 5, 2018.

UMIN Clinical Trials Registry, "Safety and efficacy of scallop-plasmalogen on patients with primary insomnia: double-blind crossover trial with Polysomnography", Mar. 2016.

Voskoglou-Nomikos et al., "Clinical Predictive Value of the in Vitro Cell Line, Human Xenograft, and Mouse Allograft Preclinical Cancer Models", Clinical Cancer Research, vol. 9, Sep. 2003, pp. 4227-4239.

Mawatari et al., Separation of intact Plasmalogens and all other phospholipids by a single run of high-performance liquid chromatography, Anal. Biochem., May 2007, pp. 54-59, 370.

Ifuku et al., Anti-inflammatory /anti-amyloidogenic effects of plasmalogens in lipopolysaccharide-induced neuroinflammation in adult mice, Journal of Neuroinflammation, Aug. 2012, pp. 1-13, 9:197.

Katafuchi et al., Effects of Plasmalogens on Systemic Lipopolysaccharide-induced Glial Activation and β-amyloid Accumulation in Adult Mice, Ann. N.Y. Acad. Sci., Jul. 2012, pp. 85-92, 1262.

Oma et al., Changes in Phospholipid Composition of Erythrocyte Membrane in Alzheimer's Disease, Dement Geriatr Cogn Disord Extra, Aug. 2012; pp. 298-303, 2.

Mawatari et al., Dietary plasmalogen increases erythrocyte membrane plasmalogen in rats, Lipids in Health and Disease, Nov. 2012, pp. 1-7, 11:161.

Hossain et al., Plasmalogens Rescue Neuronal Cell Death through an Activation of AKT and ERK Survival Signaling, PLOS One, Dec. 2013, pp. 1-14, vol. 8, Issue 12, e83508.

Fujino et al., Efficacy and Blood Plasmalogen Changes by Oral Administration of Plasmalogen in Patients with Mild Alzheimer's Disease and Mild Cognitive Impairment: A Multicenter, Randomized, Double-blind, Placebo-controlled Trial, EBioMedicine, Feb. 2017, pp. 199-205, 17.

Mawatari et al., Simultaneous Preparation of Purified Plasmalogens and Sphingomyelin in Human Erythrocytes with Phospholipases A1 from *Aspergillus orizae*; Biosci. Biotechnol. Biochem, Dec. 2009, pp. 2621-2625, 73(12).

Chelomin, V.P. et al., Alterations of microsomal lipid synthesis in gill cells of bivalve mollusc Mizuhopecten yessoensis in response to cadmium accumulation, Comparative Biochemistry and Physiology, Part C: Pharmacology, Toxicology & Endocrinology, (1991) pp. 1-5, vol. 99C, No. 1-2.

Chelomin, V.P. et al., Lipid composition and some aspects of aminophospholipid organization in erythrocyte membrane of the marine bivalve mollusc Scapharca broughtoni, Comparative Biochemistry and Physiology, Part B: Biochemistry & Molecular Biology, (1981) pp. 599-604, vol. 69B, No. 3.

Nevenzel, J.C. et al., Plasmalogens in the gill lipids of aquatic animals, Comparative Biochemistry and Physiology, Part B: Biochemistry & Molecular Biology, (1985) pp. 293-297, vol. 82B, No. 2.

Grand, F.L. et al., Membrane phospholipid composition of hemocytes in the Pacific oyster *Crassostrea gigas* and the Manila clam *Ruditapes philippinarum*, Comparative Biochemistry and Physiology, Part A: Molecular & Integrative Physiology, Apr. 2011, pp. 383-391, vol. 159A, No. 4.

Misra, S. et al., Naturally occurring etherlinked phosphatidylcholine activates phosphatidylinositol 3-kinase and stimulates cell growth, Journal of Cellular Biochemistry, May 1994, pp. 146-153, vol. 55, No. 1.

Grand, F.L. et al., Altered membrane lipid composition and functional parameters of circulating cells in cockles (*Cerastoderma edule*) affected by disseminated neoplasia, Chemistry and Physics of Lipids, Jan. 2013, pp. 9-20, vol. 167-168.

Kreps, E. et al., Phospholipids in the nervous system of molluscs, Journal of Neurochemistry, Apr. 1968, pp. 285-291, vol. 15, No. 4.

Higashi, S. et al., Role of phospholipids in the aerobic endogenous metabolism of freshwater mussel spermatozoa, Journal of Cellular Physiology, Aug. 1968, pp. 55-63, vol. 72, No. 1.

Hanus, L.O. et al., Plasmalogens, fatty acids and alkyl glyceryl ethers of marine and freshwater clams and mussels, Food Chemistry, Sep. 2009, pp. 491-498, vol. 116, No. 2.

Boselli, E. et al., Characterization of Phospholipid Molecular Species in the Edible Parts of Bony Fish and Shellfish, Journal of Agricultural and Food Chemistry, Feb. 2012, pp. 3234-3245, vol. 60, No. 12.

Kraffe, E. et al., Fatty acids of serine, ethanolamine, and choline plasmalogens in some marine bivalves, Lipids, Jan. 2004, pp. 59-66, vol. 39, No. 1.

Kraffe, E. et al., Cis-4, 7, 10, trans-13-22:4 fatty acid distribution in phospholipids of pectinid species *Aequipecten opercularis* and *Pecten maximus*, Lipids, May 2006, pp. 491-497, vol. 41, No. 5.

Grand, F.L. et al., Disseminated Neoplasia in the Soft-Shell Clam *Mya arenaria*: Membrane Lipid Composition and Functional Parameters of Circulating Cells, Lipids, Aug. 2014, pp. 807-818, vol. 49, No. 8.

Meneses, P. et al., High resolution 31P NMR of extracted phospholipids, Journal of Lipid Research, May 1988, pp. 679-689, vol. 29, No. 5.

Chebotareva, M.A. et al., Limit of change in unsaturation index of fatty acid composition of phospholipids at adaptation of molluscs to biogenic and abiogenic environmental factors, Journal of Evolutionary Biochemistry and Physiology, Oct. 2011, pp. 448-453, vol. 47, No. 5.

Joh, Y.G. et al., Studies on the lipids of abalone (11) The aldehyde composition of plasmalogen from abalone and some marine molluscs, Bulletin of the Korean Fisheries Society, (1979) pp. 181-189, vol. 12, No. 3.

Yasuda, S., Studies on the Lipids of Japanese Littleneck, *Tapes japonica* Deshayes. II. Composition of phospholipids, Yukagaku, (1967) pp. 596-600, vol. 16, No. 11.

International Search Report for Application No. PCT/JP2015/063740, dated Jul. 7, 2015.

Rodrigues, et al., "Pharmacological Interventions for Daytime Sleepiness and Sleep Disorders in Parkinson's Disease: Systematic Review and Meta-Analysis", Parkinsonism & Related Disorders, vol. 27, Jun. 2016, pp. 25-34.

Folch et al., "A Simple Method for the Isolation and Purification of Total Lipides From Animal Tissues," Journal of Biological Chemistry, vol. 226, Aug. 1956, pp. 497-509.

Chinese Search Report in First OA for Application No. 201580079798.6 dated Mar. 20, 2020, 4 pages.

(56) References Cited

OTHER PUBLICATIONS

Giovanelli et al. Surfactant-Free Polar-to-Non Polar Phase Transfer of Exfoliated MoS2 Two-Dimensional Colloids; ChemPlusChem, vol. 82, pp. 732-741. (Year: 2017).

Rapport et al. The Structure of Plasmalogens: I. Hydrolysis of Phosphatidyl Choline by Lecithinase A; Journal of Biological Chemistry, vol. 225, pp. 851-858. (Year: 1957).

* cited by examiner

FIG.3(a)Chicken breast

FIG.3(b)Clam

FIG.3(c)Corbicula

ETHER PHOSPHOLIPIDS AND METHOD FOR PRODUCING THE SAME

CROSS-REFERENCE TO RELATED APPLICATIONS

The present application is a national phase entry under 35 U.S.C. § 371 of International Application No. PCT/JP2015/063740 filed May 13, 2015, published in Japanese, which claims priority from Japanese Application No. 2014-247792 filed Dec. 8, 2014, all of which are incorporated herein by reference.

FIELD OF THE INVENTION

The present invention relates to ether phospholipids and a method for producing the same. More specifically, the present invention relates to ether phospholipids that are effective for treating and improving brain diseases such as Alzheimer's disease, Parkinson disease, depression and schizophrenia, metabolic diseases such as diabetes, various infectious diseases, and immune disorder, as well as a method for producing said ether phospholipids in an easy manner on a massive scale.

BACKGROUND OF THE INVENTION

Lipid refers to as substances that have a long fatty acid chain or a similar hydrocarbon chain in a molecule and that is present in a living body or derived from a living thing.

The lipids may be classified into storage lipids and structural lipids.

Storage lipids comprise C, H and O, and are generally soluble in acetone. Triacylglycerol that is a storage lipid is present in fat tissues of an animal body as energy storage.

On the other hand, structural lipids contain a lipid-group containing P of phosphoric acid and N of base, etc.

Thus, structural lipids comprise a hydrophobic part (fatty acid part) and a hydrophilic part (phosphoric acid and base part) to exhibit amphipathic property. Generally, while the storage lipids are soluble in acetone, structural lipids are insoluble in acetone.

Such structural lipids are structural components of a biomembrane.

The structural lipids may be roughly classified into following categories:

(1) Glycerophospholipids—examples include phosphatidylcholine (lecithin), phosphatidylethanolamine, etc.;
(2) Phosphosphingolipids—examples include sphingomyelins, ceramide ciliatine, etc.;
(3) Glycosphingolipids—examples include cerebrosides, sulfatides, gangliosides, etc.; and
(4) Glycoglycerolipids; examples include diacylglycerols existing in a microorganism or higher plants.

The above (2) phosphosphingolipids and (3) glycosphingolipids are collectively called as sphingolipids.

The glycerophospholipid is a collective term for phospholipids having a glycerol in their skeleton, examples of which include phosphatidylcholine, phosphatidylethanolamine, phosphatidylserine, etc.

Many of those glycerophospholipids are bound to a non-polar part by an ester bond (acyl bond), and some are bound at the sn-1 position of glycerol by a vinyl ether bond (alkenyl bond) or an ether bond (alkyl bond).

The former ones bound by a vinyl ether bond are also called as plasmalogens.

Glycerophospholipids having a vinyl ether bond and those having an ether bond are collectively called as ether phospholipids.

While phospholipids are important as structural components of a biomembrane, approximately 18% of phospholipids of a mammal biomembrane are plasmalogens that are ether phospholipids.

In particular, many of them are found in brain nerves, cardiac muscles, skeletal muscles, white blood cells and sperms.

Many of plasmalogens are bound to polyunsaturated fatty acids such as docosahexaenoic acids, arachidonic acids, etc.

Therefore, they play not only a role as storage of second messengers for signals between cells such as prostaglandin, leukotriene, etc., but also significant roles as cell fusion, ion transport, etc.

In addition, since a vinyl ether bond (alkenyl bond) of plasmalogens is particularly susceptible to oxidative stress, they act as an antioxidant at cell membranes.

In mammals, ether phospholipids having an alkyl bond are present although in a small amount. In particular, it is confirmed that in a rat's brain hippocampus are present phosphatidylcholine and phosphatidylethanolamine having an alkyl bond.

Furthermore, it is known that ingested phospholipids having an ether bond (alkyl bond) are transformed into plasmalogens.

These days, it is reported, as shown in WO2011/083827 (Patent Document 1), that plasmalogens-type glycerophospholipids have an effect of brain neurogenesis.

In addition, as shown in WO2012/039472 (Patent Document 2) and Ifuku et al., Journal of Neuroinflammation, 9:197 (2012) (Non-patent Document 1), it is reported that plasmalogens-type glycerophospholipids inhibit an increase of glia cells that is considered to be one of the causes triggering a central nervous system inflammation, thereby effective for improving a central nervous system inflammation, and that they are particularly effective for preventing and treating neurodegenerative disease such as Alzheimer's disease.

Further, it is reported, as shown in for example Patent Documents 1-7, that such plasmalogens-type glycerophospholipids may be obtained from a bird tissue such as chicken skin and chicken breast, in an easy manner on a massive scale.

PRIOR ART DOCUMENTS

Patent Documents

Patent Document 1 WO2011/083827 (Scope of Claims)
Patent Document 2 WO2012/039472 (Scope of Claims)
Patent Document 3 PCT/JP2008/051329 (Scope of Claims)
Patent Document 4 WO2008/146942 (Scope of Claims)
Patent Document 5 WO2009/154309 (Scope of Claims)
Patent Document 6 Japan Patent No. 5,062,873 (Scope of Patent Claims)
Patent Document 7 Japan Patent No. 5,185,539 (Scope of Patent Claims)

Non-Patent Documents

Non-patent Document 1 Ifuku et al., Journal of Neuroinflammation, 9:197 (2012)

SUMMARY OF THE INVENTION

Problem to be Solved by the Invention

Production methods disclosed in the Patent Documents 1-7 are methods for producing plasmalogens-type glycerophospholipids from a bird tissue such as chicken skin or chicken breast in an easy manner on a massive scale.

In particular, Patent Document 4 discloses a method for producing plasmalogens-type glycerophospholipids from chicken breast in an easy manner on a massive scale as compared to then conventional ones from chicken skin.

However, it had been constantly sought any superior plasmalogens-type glycerophospholipids or ether phospholipids to the conventional ones and a method for producing the same in an easy manner on a massive scale, in light of effects of treating and improving brain diseases such as Alzheimer's disease, Parkinson disease, depression and schizophrenia, metabolic diseases such as diabetes, various infectious diseases, and immune disorders.

Under such circumstances, the present inventors have studied for an objective to provide plasmalogens-type glycerophospholipids or ether phospholipids that are significantly superior to the conventional ones in light of the above effects, as well as a method for producing the same in an easy manner on a massive scale.

As a consequence, the present inventors found that ether phospholipids obtained from bivalve tissues, preferably by being provided a certain process, exhibit significantly superior effects of the above effects as compared to the conventional plasmalogens-type glycerophospholipids derived from chicken tissues. The present invention was so completed.

Solution to the Problem

The present invention according to one embodiment provides, ether phospholipids that are obtained from a bivalve tissue by extraction processing.

The present invention according to one embodiment is characterized in, the ether phospholipids containing the one presented by the following formula (1) and/or (2).

[Chemical Formula 1]

(1)

$CH_2O—CH=CHR^1$ (sn-1)
$CH—O—CO—R^2$ (sn-2)
$CH_2OPO_3—X$ (sn-3)

[Chemical Formula 2]

(2)

$CH_2O—CH—CHR^1$ (sn-1)
$CH—O—COR^2$ (sn-2)
$CH_2OPO_3—X$ (sn-3)

In the above formulas,
$R^1$ represents an aliphatic hydrocarbon group having 14 to 18 carbon numbers.
$R^2$ represents mainly eicosapentaenoic acid, docosahexaenoic acid or arachidonic acid, wherein it is preferred that those three kinds of fatty acids account for 50% or higher of the total fatty acids.

X represents mainly ethanolamine or choline, wherein it is preferred that their total accounts for 90% or higher of the total phospholipids.

The present invention according to one embodiment is characterized in,
a method for producing ether phospholipids derived from bivalve tissues comprising:
(A) a step of processing total lipids of bivalve tissues with a water-soluble ketone solvent to get bivalve phospholipids without neutral fat;
(B) a step of providing extraction processing from the bivalve phospholipids without neutral fat obtained by the step (A) with a hydrophobic organic solvent to get glycerophospholipids; and
(C) a step of reacting the glycerophospholipids obtained by the step (B) with phospholipase A1 to decompose mixed diacyl-glycerophospholipids, followed by solution partitioning (e.g., a partitioning method by extracting lipids to hexane layer to separate with acetone or water) etc. to get s purified ether phospholipid.

The present invention according to one embodiment is characterized in,
wherein the hydrophobic organic solvent is ether or petroleum ether.

The present invention according to one embodiment is characterized in,
wherein the water-soluble ketone solvent is acetone.

The present invention according to one embodiment is characterized in,
a method for producing ether phospholipids derived from bivalve tissues comprising:
(D) a step of extracting total lipids from bivalve tissues with a non-polar organic solvent and branched alcohol mixture; and
(E) a step of reacting the total lipids obtained by the step (D) with phospholipase A1 to hydrolyze diacyl phospholipids mixed therein, followed by solvent partition etc. to get a purified ether phospholipid.

The present invention according to one embodiment provides,
ether phospholipids derived from bivalve tissues that is characterized in being obtained by the method for producing the same.

The present invention according to one embodiment provides,
a beverage and/or food product that is characterized in containing ether phospholipids disclosed herein.

The present invention according to one embodiment provides,
a pharmaceutical composition that is characterized in containing ether phospholipids disclosed herein.

Effects of the Invention

According to the present invention, ether phospholipids obtained from bivalve tissues exhibit the significant superiority of function and effect for treating and improving brain diseases such as Alzheimer's disease, Parkinson disease, depression and schizophrenia, metabolic diseases such as diabetes, various infective diseases, and immune disorders.

And ether phospholipids with such a function and effect may be produced from bivalves in an easy manner on a massive scale.

BRIEF DESCRIPTION OF THE DRAWINGS

FIG. 1 shows HPLC charts, where

FIG. 2 shows HPLC charts, where

FIG. 3 shows HPLC charts, where

DESCRIPTION OF EMBODIMENTS

The followings describe embodiments to exercise the present invention, ether phospholipids and a method for producing the same.

Although the present invention is described mainly by preferred representative examples, the present invention is not limited to such examples.

According to the present invention, the ether phospholipids are obtained by extraction processing from bivalve tissues.

Here, ether phospholipid represents glycerophospholipid that has a vinyl ether bond (alkenyl bond) or an ether bond (alkyl bond) at the $1^{st}$ position of the glycerol backbone (sn-1). General formulas of ether phospholipid are described below. A compound represented by the formula (1) is alkenyl phospholipid (plasmalogens), while a compound represented by the formula (2) is alkyl phospholipid.

In the above formulas, $R^1$ represents an aliphatic hydrocarbon group.

$R^1$ is usually an aliphatic hydrocarbon group having 14 to 18 carbon numbers.

$R^2$ represents an aliphatic hydrocarbon group, which is often cases bound to polyunsaturated fatty acid, such as arachidonic acid (ARA), docosahexaenoic acid (DHA), eicosapentaenoic acid (EPA), and the like.

Further, X represents a polar group in the above formulas.

Preferably, X is ethanolamine, choline, serine, inositol, etc.

In particular, ether phospholipids present in a mammal contain mainly ethanolamine plasmalogens in which X in the above formulas is ethanolamine and choline plasmalogens in which X is choline.

Ingested glycerophospholipids having an ether bond (alkyl bond) are absorbed in the original form to be used in each tissue, or are transformed inside a body into alkenyl bond-type phospholipids (plasmalogens).

According to the present invention, a bivalve used therein may be, for example, a clam, corbicula, giant clam, scallop, oyster, etc.

The bivalve tissue may be, for example, an internal organ, gonad, muscle, etc.

According to the present invention, a method for extracting ether phospholipids from said bivalve tissue is not be limited in particular, as long as the method can extract (and purify if necessary) ether phospholipids.

Preferably, ether phospholipids may be extracted and purified by a method comprising:

(A) a step of processing total lipids of bivalve tissues with water-soluble ketone solvent to remove neutral fat to get bivalve phospholipids without neutral fat;

(B) a step of further extracting total glycerophospholipids from the bivalve phospholipids without neutral fat obtained by the step (A) with a hydrophobic organic solvent, and concentrating if necessary; and (C) a step of reacting the total glycerophospholipids obtained by the step (B) with phospholipase A1 to hydrolyze mixed diacyl-glycerophospholipids, followed by solution partitioning (solvent partitioning method) to remove a degradation product (such as lyso type phospholipids or free fatty acids).

According to the above method, the step (C) represents a step of purifying ether phospholipids.

Although such a step is not necessarily included, it is more preferred since purified and concentrated ether phospholipids may have far superior effects.

In the said step (A), it removes neutral fat from total lipids of bivalve tissues.

Preferably, the bivalve tissue is minced or ground in advance before the use.

Examples of the water-soluble ketone solvent include acetone and/or methyl ethyl ketone, and preferably acetone is selected.

It is not particularly difficult to get total lipids, as they can be obtained by providing extraction processing in accordance with a conventional method using a solvent such as isopropanol, hexane, etc.

The said step (B) is to extract total glycerophospholipids from the bivalve phospholipids without neutral fat obtained by the step (A) with a hydrophobic organic solvent.

As the organic solvent, ether or petroleum ether may be selected.

The said step (C) is to remove diacyl-type phospholipids by hydrolyzing diacyl-type glycerophospholipids mixed within the total glycerophospholipids obtained by the step (B).

For the above hydrolysis, phospholipase A1 (PLA1) is used.

This PLA1 specifically hydrolyzes an acyl bond at the sn-1 of diacyl-type phospholipids.

Therefore, PLA1 does not act on an ether bond at the sn-1 of ether phospholipids.

By the PLA1 processing, diacyl-glycerophospholipids are decomposed into free fatty acids and lyso phospholipids.

Free fatty acids and lyso phospholipids may be removed by harnessing their nature of being relatively water-soluble.

The PLA1 is not particularly limited to its derivation, as long as it can attain the above effect.

The exemplary PLA1 may be the one derived from *Aspergillus orizae*.

Such PLA1 may be purchased from Mitsubishi Kagaku Foods Corporation.

The amount of the PLA1 used may be selected as deemed fit, depending on the amount of the total glycerophospholipids.

The amount per 1 g of the total glycerophospholipids is preferably 0.15-0.45 g, more preferably 0.2-0.3 g.

Enzyme reaction by the PLA1 may be performed in a buffer. Such a buffer may be selected as deemed fit depending on PLA1 used.

For example, 0.1M citric acid-HCl buffer (pH4.5) may be used.

In that case, the total glycerophospholipids may be added by the buffer to dissolve, subsequently PLA1 may be added.

Although there is no particular restriction as to the amount of the buffer used as long as enzyme reaction can be progressed, the amount per Ig of the total glycerophospholipids is preferably 1-30 mL, more preferably 5-15 mL.

The reaction conditions can be selected as deemed fit.

The reaction is run preferably at the temperature of 30-70° C., more preferably at 45-55° C., further preferably at 50° C. Stirring is provided during the reaction. The reaction time is preferably 1-5 hours, more preferably 1-2 hours.

Then used pH is preferably pH3.5-5.5, more preferably pH4-5.

The enzyme reaction may be stopped by cooling.

In addition, deactivation treatment of enzyme may be performed.

For example, the deactivation treatment may be performed by increasing the temperature to around 70° C., subsequent to the hydrolysis reaction.

Accordingly, a process liquid (hydrolysis process liquid) may be obtained wherein diacyl-type glycerophospholipids are decomposed.

To the hydrolysis process liquid, for example, hexane is added in the double or triple amount, then a liquid layer is separated. By doing so, an enzyme buffer and enzyme protein may be removed.

Furthermore, since ether phospholipids are soluble in hexane but are hardly soluble in a water-soluble ketone series solvent, ether phospholipids may be purified by performing a partition combining these solvents and water as deemed fit, further performing a solution partition by water or water-solution (solvent partition method) to remove lyso phospholipids.

In other words, a water-soluble ketone series solvent such as acetone enables to remove neutral fat other than phospholipids, and to separate between ether phospholipids and lyso phospholipids by a waterborne solution partition.

According to the present invention, ether phospholipids may be extracted and purified by a method comprising:

(D) a step of extracting total lipids from bivalve tissues with a non-polar organic solvent and branched alcohol mixture; and (E) a step of reacting the total lipids obtained by the step (D) with phospholipase A1 to hydrolyze diacyl phospholipids mixed therein, followed by solvent partition etc. to get a purified ether phospholipid.

According to the present invention, it is preferred to select such a method, because it can be performed in an easy and convenient manner.

Examples of the non-polar organic solvent include saturated fat series carbon hydride class, is selected preferably straight-chain saturated hydrocarbon, more preferably hexane.

Examples of the branched alcohol include secondary alcohol and tertiary alcohols, is selected preferably secondary alcohols, more preferably isopropanol.

In that case, by the above step (E), a process liquid may be obtained wherein diacyl phospholipids are decomposed. To the hydrolysis process liquid, for example, added is hexane-isopropanol mixture (3:2) that is diluted by 5-10 times, to be placed into a separating funnel. It is then added by the approximately ⅔ amount of water to separate bilayer, and the upper layer (hexane layer) is recovered. By doing so, a lipid decomposed product (free fatty acid, lyso phospholipid), enzyme protein and enzyme buffer may be removed.

Such a method may be easily performed in reference to the aforementioned extraction and purification method of ether phospholipids.

According to the present invention, ether phospholipids derived from bivalve tissues contain mainly ethanolamine phospholipids and choline phospholipids.

The structure of such lipids may be analyzed and confirmed using High-Performance Liquid Chromatography (HPLC).

According to the present invention, ether phospholipids derived from bivalve tissues are bound at the sn-2 position to a number of docosahexaenoic acid (DHA), arachidonic acid (ARA) and eicosapentaenoic acid (EPA).

In other words, they contain one or more of the kinds as residue selected from a group comprising docosahexaenoyl group, arachidonoyl group and eicosapentaenoyl group.

Such a structure enables ether phospholipids derived from bivalve tissues according to the present invention to be significantly effective for treating and improving brain diseases such as Alzheimer's disease, Parkinson disease, depression and schizophrenia, metabolic diseases such as diabetes, various infectious diseases, and immune disorders.

According to the present invention, ether phospholipids derived from bivalve tissues may be applied to a beverage and food product as a material and to a pharmaceutical composition as an ingredient.

Since the ether phospholipids are effective for treating and improving brain diseases such as Alzheimer's disease, Parkinson disease, depression and schizophrenia, metabolic diseases such as diabetes, various infectious diseases, and immune disorders, such effects may be achieved by ingesting them into a living body.

Further according to the present invention, ether phospholipids derived from bivalve tissues may be applied not only to the above publicly known product forms, but to various product forms that would be developed in the future, as deemed fit.

Similarly, they may be applied to a form of functional foods or that of specified health foods.

The exemplary form of beverage and food products includes a sweet (such as frozen dessert, jelly, cake, candy, chewing gum, etc.), bread, dairy product such as milk, yogurt, etc., and other various products.

By using a seasoning agent and/or sweetening agent that may be used in a beverage and food product, they may be applied in a form of beverage as a liquid solution.

Similarly, while the functional foods and specified health foods (including nutritional supplement) contain ether phospholipids derived from bivalve tissues according to the present invention, the form may be varied not only in a form of a beverage and food product, but in a form of a drug formulation for oral ingestion, such as a tablet (including sugar-coated tablet, film-coated tablet), powder medicine, granular tablets, encapsulated formulation (including soft capsule), syrup, liquid form (such as juice), etc.

For example, such products may be produced by adding the ether phospholipids to fruit juice, dairy products such as milk and yogurt, excipients such as lactose and dextrin, and other materials for general health foods, although not limited to them.

In the case of selecting a supplement form that is one form of functional foods, any publicly-known methods may be used.

For example, to the ether phospholipids as an active ingredient, added is excipient (lactose, sucrose, starch, etc.), disintegrant (starch, calcium carbonate, etc.), binder (starch, gum arabic, carboxymethylcellulose, polyvinylpyrrolidone, hydroxypropylcellulose, etc.) or lubricant (talc, magnesium stearate, polyethyleneglycol 6000, etc.) and the like, to provide compression formation.

In addition, as deemed necessary, coating may be provided by a publicly known measure for the purposes of taste masking, enteric function or long-acting function.

Since such food products contain the ether phospholipids as well, they also achieve treatment and improvement effects on brain diseases such as Alzheimer's disease, Parkinson disease, depression and schizophrenia, metabolic diseases such as diabetes, various infectious diseases, and immune disorders.

Although it is easy and convenient to use the ether phospholipids by mixing them into any products, it is as a matter of course that a certain amount of the ether phospholipids is required to achieve the above effects. For example, a beverage and food product contains the ether phospholipids preferably in the amount of approximately 0.01-80 mass %, more preferably in the amount of approximately 0.05-20 mass %.

With regards to beverage and food products, the intake amount of the ether phospholipids as active ingredients may be selected as deemed fit depending on a subject's age, weight, diathesis, physical condition, morphology, ingestion period, etc.

Such beverage and food products may be used, for preventive purpose, not only by a healthy individual but to a patient with a variety of diseases from severe to mild levels, not limited in particular to metabolic diseases or Alzheimer's disease.

According to the present invention, the ether phospholipids derived from bivalve tissues may be administered orally to a patient as a medicament decomposed or suspended in diluent, and if necessary by combining them with a pharmaceutically acceptable carrier.

According to the present invention, a pharmaceutical composition may be obtained by properly mixing with a proper additive, for example:

excipient such as lactose, sucrose, maize starch, synthesis or natural gas, crystalline cellulose, etc.;

binder such as starch, cellulose derivative, gum arabic, gelatin, polyvinylpyrrolidone, etc.;

disintegrant such as carboxymethylcellulose calcium, carboxymethylcellulose sodium, starch, corn starch, alginate sodium, etc.;

lubricant such as talc, magnesium stearate, sodium stearate, etc.;

filler or diluent such as calcium carbonate, sodium carbonate, calcium phosphate, sodium phosphate, etc.

and the like to form a tablet, powder medicine, ball, granular tablet, etc.

It may take encapsulated formulation by using a hard or soft gelatin capsule.

In addition, according to the present invention, a pharmaceutical composition may be obtained by dissolving the ether phospholipids into a generally used inert diluent such as purified water, and if necessary by adding to the solution a proper additive such as wetting-out agent, emulsifier, dispersion assistant, surfactant, sweetener, flavor, fragrance substance, etc. to form a liquid medicament such as syrup, elixir, etc.

Such a medicament may be produced by a conventional, publicly known method.

According to the present invention, in the case where then obtained pharmaceutical composition is administered to a human as a medicine, the dosage amount is determined based on the dosage amount of a specified compound as an active ingredient.

Such a dosage amount is within the range of 1-1,000 mg although it depends on a dosage form, patient's age, etc. Preferably, the dosage amount to an adult with weight 50 kg is 10-500 mg per day.

The present invention may be also applied to an animal other than a human in a form of feedstuff, medicine, pharmaceutical composition, etc.

EXAMPLES

The followings describe the present invention with reference to examples in details on ether phospholipids and a method for producing the same. However, the present invention is not limited to these examples.

Example 1

(Production of Ether-Type Glycerophospholipids Derived from Bivalves)
(1) Extraction of Bivalves Total Lipids To 100 g of bivalve clams, 200 mL of isopropanol and 300 mL of hexane were added, ground by a blender, and placed in static standing for 1 hour at a room temperature.

Subsequently, suction filtration was provided, and its filtrate was placed in a separating funnel.

The separating funnel was added by 360 mL of water and mixed.

Figure 1A:
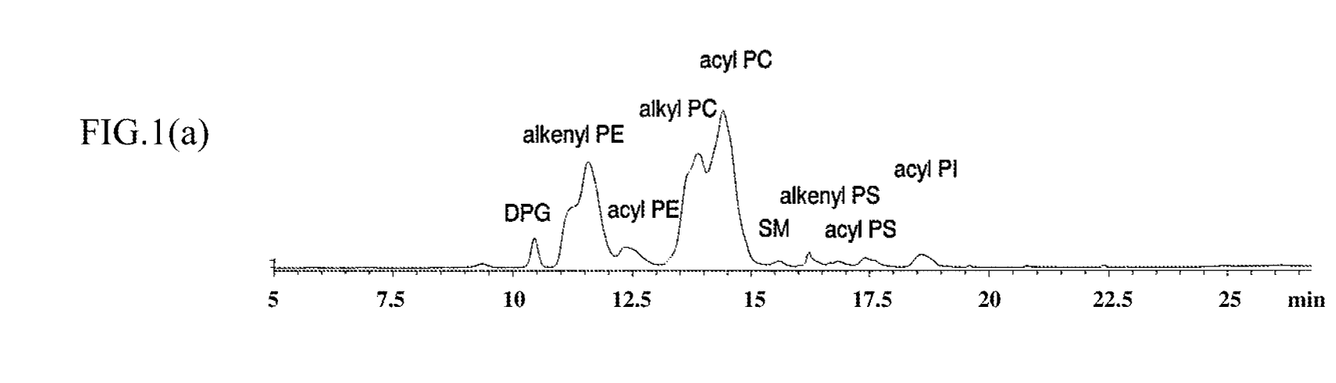
FIG. 1(a) is an HPLC chart depicting the total phospholipids derived from a bivalve (clam)

An upper hexane layer was separated then dried, and total bivalve lipids were obtained.
(2) Extraction of Total Phospholipids from Total Lipids To the total lipids so obtained, 200 mL of acetone was added and stirred. The mixture was stored in ice, and then was centrifuged 1000×g for 10 minutes at a temperature of 4° C. Its precipitation was separated, and total bivalve phospholipids without neutral fat were obtained.
(3) Analysis of Clam-Derived Total Phospholipids by HPLC HPLC was performed on the total phospholipids so obtained under the following conditions.

The result is shown in FIG. 1(a).
<Conditions for HPLC>

Device used: HPLC Agilent 1100 System (Agilent Technologies, Tokyo)

Column: Lichrosphere 100 Diol (250*3 m, 5 μm) (Agilent Technologies)

Flow rate: 0.8 ml/min

Detection: ELSD (evaporative light scattering detection) (Agilent

Technologies)

Mobile Phases:

(A) Hexane/isopropanol/acetic acid (82:17:1, v/v, 0.08% TEA*)

(B) Isopropanol/water/acetic acid (85:14:1, 0.08% TEA*)

*TEA refers to triethylamine.

TABLE 1 shows a gradient of time zone and mobile phases (A) and (B).

TABLE 1

| Time (min.) | Mobile phase (A) (%) | Mobile phase (B) (%) |
|---|---|---|
| 0 | 95 | 5 |
| 21 | 40 | 60 |
| 25 | 15 | 85 |
| 26 | 15 | 85 |
| 29 | 95 | 5 |
| 34 | 95 | 5 |

(4) Separation of Total Glycerophospholipids

The total phospholipids (acetone precipitation) so obtained was dissolved into 50 mL of ether and mixed. Thereafter the mixture was centrifuged 1000×g for 10 minutes at a temperature of 4° C. Its supernatant (ether layer) was then dried, and total glycerophospholipids were obtained.

(5) Purification of Ether Phospholipids by Enzyme Treatment and Extraction Processing of Total Glycerophospholipids The total glycerophospholipids so obtained were dispersed in 20 mL of phospholipase A1 (Mitsubishi Chemical Foods Corporation) solution (20 mg/mL, citrate buffer solution (pH4.5)), well mixed using ultra sonic waves, etc., and then was kept for the reaction to run at a temperature of 50° C. for 2 hours.

Subsequently, the mixture was cooled and stopped reaction.

Then added was 400 mL of hexane/isopropanol (3:2), which was then placed in a separating funnel, mixed, added 240 mL of water, and placed in static standing, then a water layer was removed.

In order to remove remaining lyso-type phospholipids, the remaining hexane layer was added by 200 mL of water, then mixed, after which the hexane layer was separated and dried.

In order to further remove remaining neutral fat, the resulting mixture was added by 100 mL of acetone, mixed, cooled, and then centrifuged to separate precipitation. Accordingly, purified ether-type glycerophospholipids derived from bivalves were obtained.

(6) HPLC Analysis of Bivalve-Derived Purified Ether Phospholipids (Ether-Type Glycerophospholipids)

Figure 1B:
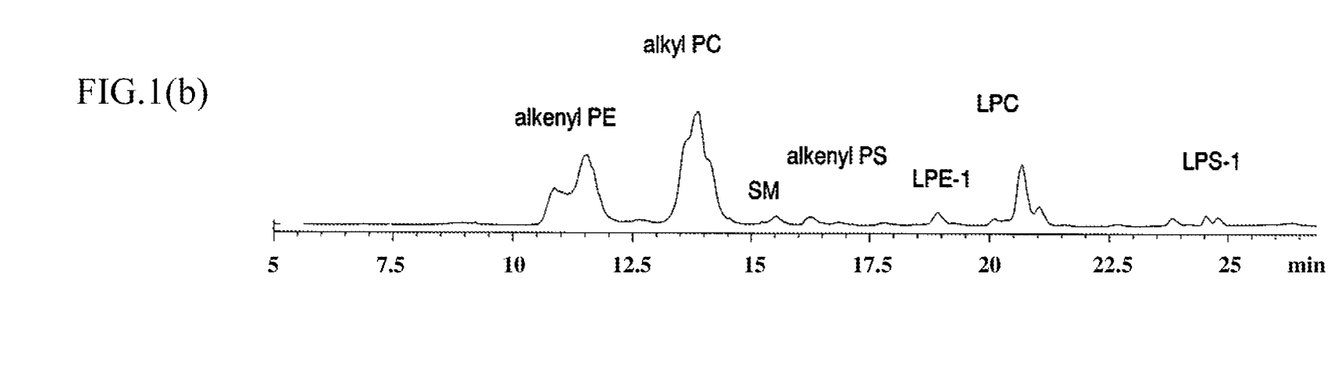
FIG. 1(b) is an HPLC chart depicting the ether phospholipids derived from a purified bivalve (clam).

HPLC analysis was provided on the ether-type glycerophospholipids derived from bivalves (clam) so obtained under the above conditions. The result is shown in FIG. 1(b).

Example 2

(Production of Ether Phospholipids Derived from Bivalves)

(1) Separation of Bivalve Fractured Tissues without Neutral Fat and Extraction of Total Glycerophospholipids Except that corbicula was used instead of clam as a bivalve, total glycerophospholipids were obtained by the method similar to EXAMPLE.

(2) HPLC Analysis of Corbicula-Derived Total Phospholipids

Figure 2A:
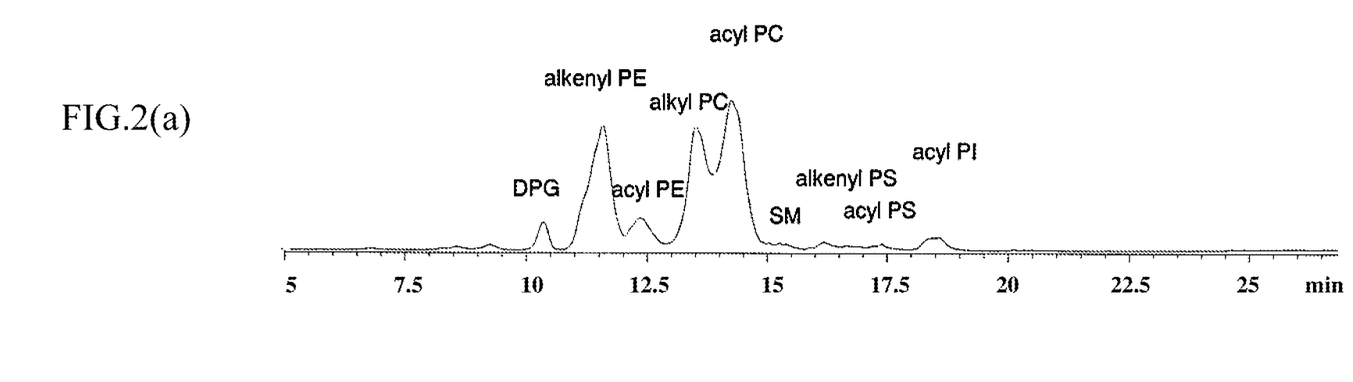
FIG. 2(a) is an HPLC chart depicting the total phospholipids derived from a bivalve (corbicula)

HPLC analysis was provided on the total phospholipids so obtained under the conditions similar to EXAMPLE 1. The result is shown in FIG. 2(a).

(3) Purification of Ether Phospholipids by Enzyme Treatment and Extraction Processing of Total Glycerophospholipids By using the similar method of EXAMPLE 1, ether-type glycerophospholipids are purified by preparing corbicula-derived ether-type glycerophospholipids.

(4) HPLC Analysis of Purified Bivalve-Derived Ether Phospholipids

Figure 2B:
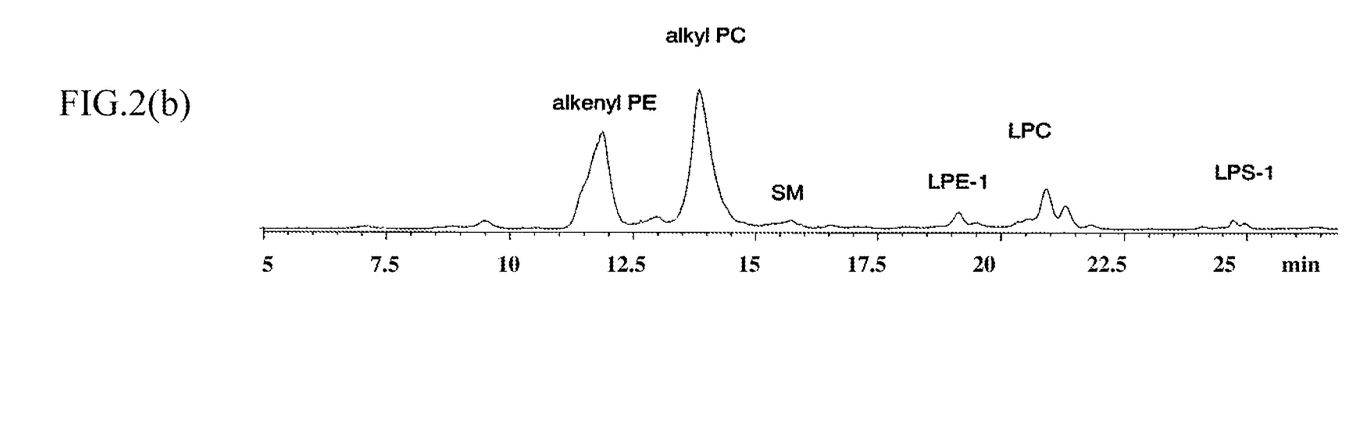
FIG. 2(b) is an HPLC chart depicting the ether phospholipids derived from a purified bivalve (corbicula).

HPLC analysis was provided on the bivalve-derived ether phospholipids so obtained under the conditions similar to EXAMPLE 1.

The result is shown in FIG. 2(b).

Example 3

(Production of Ether Phospholipids Derived from Bivalves)

(1) Extraction of Total Lipids from Bivalves

To 100 g of bivalve clams, 500 mL of the hexane/isopropanol mixture (3:2) was added, ground by a blender, and placed for 1 hour at a room temperature while mixing.

Subsequently, suction filtration was provided, and its residue was washed by 200 mL of hexane/isopropanol mixture (3:2) and added to the filtrate, which was then placed in a separating funnel.

To the separating funnel, 400 mL of water was added and mixed, then placed in static standing.

Out of two separate layers, the lower layer was removed, and the upper hexane layer was separated.

The hexane layer so obtained was dried, and total bivalve lipids were obtained.

(2) Purification of Ether Phospholipids by Enzyme Treatment and Extraction Processing of Total Lipids The total lipids so obtained were dispersed in 20 mL of phospholipase A1 (Mitsubishi Chemical Foods Corporation) solution (20 mg/mL, citrate buffer solution (pH4.5)), well mixed using ultra sonic waves, etc., to react at a temperature of 50° C. for 2 hours.

Subsequently, the mixture was cooled and stopped reaction.

Then added was 360 mL of hexane/isopropanol (3:2), which was then placed in a separating funnel, mixed, added 220 mL of water, and placed in static standing, then a water layer was removed.

The hexane layer was separated and dried.

In order to remove remaining neutral fat such as cholesterol, the resulting mixture was added by 20 mL of acetone, mixed, ice cooled, and then centrifuged at a temperature of 10° C. for 10 minutes to separate precipitation. Accordingly, purified bivalve-derived ether phospholipids were obtained.

Example 4

(Production and Analysis of Various Bivalve-Derived Total Glycerophospholipids)

By using the method similar to EXAMPLE 1, total glycerophospholipids were obtained from various kinds of bivalves.

HPLC analysis was then provided on those total glycerophospholipids so obtained under the conditions similar to EXAMPLE 1.

The result is shown in TABLE 2.

TABLE 2

Composition of Glycerophospholipids in Various Bivalve Tissues (%)

| | Clam | Corbicula | Oyster | Scallop (mantle part) | Scallop (adductor part) |
|---|---|---|---|---|---|
| DPG | 2.2 | 2.9 | 4.8 | 2.8 | 1.1 |
| Alkenyl PE | 27.4 | 25.7 | 23.6 | 27.6 | 19.8 |
| Acyl PE | 4.4 | 6.5 | 4.4 | 7.1 | 10.3 |
| Alkyl PC | 24.9 | 23.5 | 15.2 | 16.6 | 11.6 |
| Acyl PC | 34.3 | 33.1 | 42.4 | 36.6 | 49.8 |

TABLE 2-continued

Composition of Glycerophospholipids in Various Bivalve Tissues (%)

|  | Clam | Corbicula | Oyster | Scallop (mantle part) | Scallop (adductor part) |
|---|---|---|---|---|---|
| Alkenyl PS | 2.3 | 2.4 | 2.9 | 0.5 | 1.6 |
| Acyl PS | 1.6 | 1.3 | 2.3 | 3.5 | 2.1 |
| Acyl PI | 2.2 | 3.1 | 2.0 | 1.8 | 2.0 |
| Total ether phospholipids | 54.6 | 51.4 | 41.9 | 44.6 | 29.6 |

Notes:
DPG = Cardiolipin (Diphosphoglyceride)
PE = Ethanolamine phospholipid
PC = Choline phospholipid
PS = Serine phospholipid
PI = Inositol phospholipid It was found that approximately 30% of total glycerophospholipids comprised ethanolamine phospholipids (PE), of which approximately 90% comprised plasmalogens (alkenyl PE).

It was further found that approximately 50% of total glycerophospholipids comprised choline phospholipids (PC), of which approximately 35% comprised alkyl PC.

In bivalve tissues, approximately 30-55% of total glycerophospholipids comprises ether phospholipids.

Example 5

(Analysis of Polyunsaturated Fatty Acids within Total Fatty Acids of Ether Phospholipids)

Figure 3A:
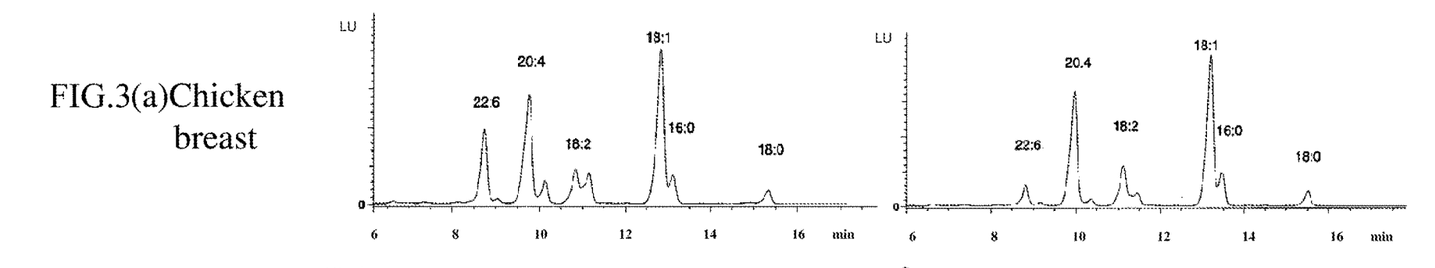
FIG. 3(a) is an HPLC chart depicting composition percentage of polyunsaturated fatty acids per total fatty acids in ether phospholipids derived from a chicken breast.
Figure 3B:
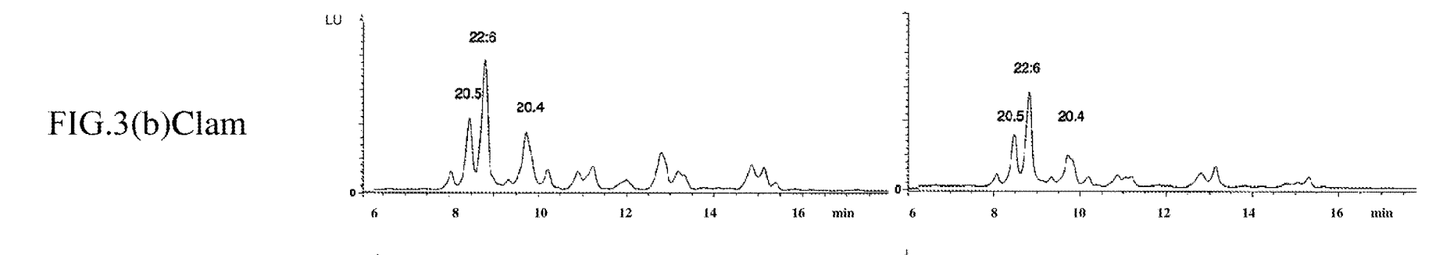
FIG. 3(b) is an HPLC chart depicting composition percentage of polyunsaturated fatty acids per total fatty acids in ether phospholipids derived from a clam.
Figure 3C:
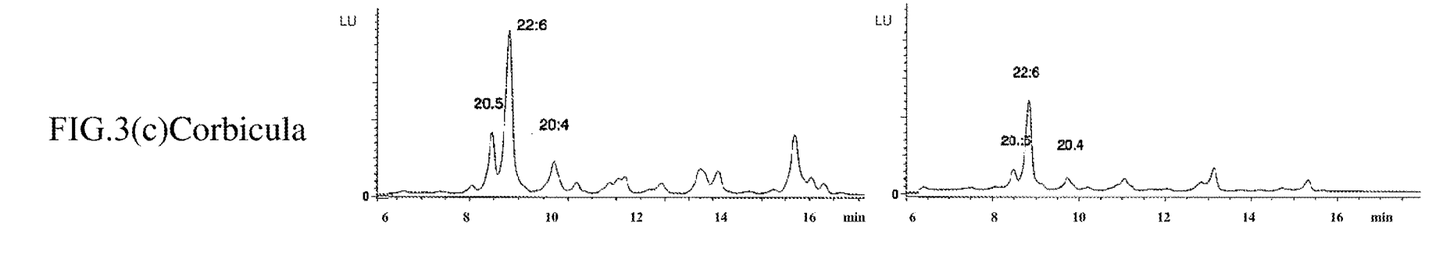
FIG. 3(c) is an HPLC chart depicting composition percentage of polyunsaturated fatty acids per total fatty acids in ether phospholipids derived from a corbicula.

An analysis using HPLC was provided with regards to the ratio of polyunsaturated fatty acids (EPA, DHA and ARA) within total fatty acids contained in bivalve-derived ether phospholipids and chicken-derived ether phospholipids, according to the following method. The results are shown in TABLES 4 and 5 and FIG. 3.

(Hydrolysis of Various Bivalve-Derived Ether Phospholipids)

Various kinds of bivalve-derived ether phospholipids were separately obtained and dried, which was hydrolyzed with methanol solution of a determined 0.5 potassium hydroxide. Accordingly, free fatty acids were obtained.

(Label for Free Fatty Acids from Various Bivalve-Derived Ether Phospholipids)

Free fatty acids produced by hydrolysis from the ether phospholipids were then labeled by 0.05% 9-anthryldiazomethane (ADAM).

(Analysis of Fatty Acids)

HPLC analysis was provided on the fatty acids so labelled under the following conditions.

<Conditions of HPLC>:

Device used: HPLC Agilent 1100 System (Agilent Technologies)

Column: Ultrasphere 100 RP-18e (Merck);

Flow rate: 0.8 ml/min

Detection: Fluorometric detector

Mobile Phases:

(A) Acetonitrile (B) Ethanol (C) Hexane

TABLE 3 shows a liquid composition in terms of time zone and mobile phases (A) to (C).

TABLE 3

| Time (min.) | Mobile phase (A) (%) | Mobile phase (B) (%) | Mobile phase (C) (%) |
|---|---|---|---|
| 0 | 100 | 0 | 0 |
| 16 | 44 | 32 | 24 |
| 16.1 | 100 | 0 | 0 |
| 24 | 100 | 0 | 0 |

TABLE 4

Polyunsaturated Fatty Acids within Total Fatty Acids of Various Ether Phospholipids

|  | Clam Alkenyl PE | Corbicula Alkenyl PE | Chicken Breast Alkenyl PE |
|---|---|---|---|
| EPA (20:5) | 11.1 | 12.1 | — |
| DHA (22:6) | 31.8 | 23.2 | 14.7 |
| ARA (20:4) | 8.5 | 15.2 | 23.6 |

EPA eicosapentaenoic acid
DHA docosahexaenoic acid
ARA arachidonic acid

TABLE 5

Polyunsaturated Fatty Acids within Total Fatty Acids of Various Ether Phospholipids

|  | Clam Alkyl PC | Corbicula Alkyl PC | Chicken Breast Alkenyl PC |
|---|---|---|---|
| EPA (20:5) | 10.5 | 15.1 | — |
| DHA (22:6) | 37.4 | 25.5 | 5.6 |
| ARA (20:4) | 8.3 | 8.7 | 29.2 |

EPA eicosapentaenoic acid
DHA docosahexaenoic acid
ARA arachidonic acid

According to TABLES 4 and 5 as well as FIG. 3, it is found that bivalve-derived ether phospholipids are bound, at the sn-2 position, to a large amount of eicosapentaenoic acid (EPA), and docosahexaenoic acid (DHA).

On the other hand, with regards to chicken breast-derived ether phospholipids that were analyzed simultaneously by the same method as the bivalve-derived ether phospholipids, both PE and PC are alkenyl phospholipids and no alkyl PC is present.

Therefore, by comparing the compositions of fatty acids, it was demonstrated that bivalve-derived ether phospholipids contain EPA and DHA in a larger amount.

EPA and DHA are decreased in brain diseases such as Alzheimer's disease, Parkinson disease, depression and schizophrenia, metabolic diseases such as diabetes, various infectious diseases, and immune disorders. In addition, EPA functions to store prostaglandin and DHA functions to store neuroprotectin.

While bivalve-derived ether phospholipids contain EPA and DHA in a large amount, chicken breast-derived ether phospholipids do not contain EPA at all and do contain DHA yet in a small amount.

Therefore, according to the present invention, since bivalve-derived ether phospholipids contain a larger amount of eicosapentaenoic acid (EPA), and docosahexaenoic acid (DHA), it is expected to achieve superior effects as compared to the conventional ether phospholipids.

INDUSTRIAL UTILITY

According to the present invention, it enables to produce ether phospholipids in an easy manner on a massive scale, that are effective for treating and improving brain diseases such as Alzheimer's disease, Parkinson disease, depression and schizophrenia, metabolic diseases such as diabetes, various infectious diseases, and immune disorders. Therefore, the present invention may be applied widely in the medicinal industry.

The invention claimed is:

1. A method for producing ether phospholipids derived from bivalve tissues comprising:
   (A) a step of processing total lipids of bivalve tissues with water-soluble ketone solvent to get bivalve phospholipids without neutral fat;
   (B) a step of providing extraction processing from the bivalve phospholipids without neutral fat obtained by the step (A) with ether or petroleum ether to get a glycerophospholipid; and
   (C) a step of reacting the glycerophospholipids obtained by the step (B) with phospholipase A1 to decompose mixed diacyl-glycerophospholipids, followed by solution partitioning to get a purified ether phospholipid.

2. The method for producing ether phospholipids derived from bivalve tissues according to claim 1, wherein the water-soluble ketone solvent is acetone.

3. Ether phospholipids derived from bivalve tissues obtained by the method for producing the same according to claim 1.

4. Ether phospholipids derived from bivalve tissues obtained by the method for producing the same according to claim 2.

5. A beverage and/or food product containing ether phospholipids according to claim 3.

6. A beverage and/or food product containing ether phospholipids according to claim 4.

7. A pharmaceutical composition containing ether phospholipids according to claim 3.

8. A pharmaceutical composition containing ether phospholipids according to claim 4.

* * * * *